(12) United States Patent
Fahrni et al.

(10) Patent No.: US 9,810,675 B2
(45) Date of Patent: Nov. 7, 2017

(54) SYSTEM AND METHOD FOR NON-INVASIVELY AND NON-DESTRUCTIVELY AUTHENTICATING BOTTLED BEVERAGES

(71) Applicant: The Regents of the University of California, Oakland, CA (US)

(72) Inventors: Simon M. Fahrni, Irvine, CA (US); Benjamin T. Fuller, Auburn, CA (US)

(73) Assignee: The Regents of the University of California, Oakland, CA (US)

( * ) Notice: Subject to any disclaimer, the term of this patent is extended or adjusted under 35 U.S.C. 154(b) by 62 days.

(21) Appl. No.: 14/772,992

(22) PCT Filed: Mar. 15, 2013

(86) PCT No.: PCT/US2013/032419
§ 371 (c)(1),
(2) Date: Sep. 4, 2015

(87) PCT Pub. No.: WO2014/143026
PCT Pub. Date: Sep. 18, 2014

(65) Prior Publication Data
US 2016/0018375 A1 Jan. 21, 2016

(51) Int. Cl.
*G01N 33/14* (2006.01)
*G01N 1/22* (2006.01)
(Continued)

(52) U.S. Cl.
CPC ......... *G01N 33/146* (2013.01); *G01N 1/2226* (2013.01); *G01N 2030/009* (2013.01)

(58) Field of Classification Search
CPC ........ G01N 33/14; G01N 33/146; G01N 1/22; G01N 1/2226; G01N 1/24; G01N 2030/009
See application file for complete search history.

(56) References Cited

U.S. PATENT DOCUMENTS

| | | | |
|---|---|---|---|
| 6,541,260 B1 * | 4/2003 | Pariseau | G01N 33/146 422/28 |
| 7,012,427 B2 | 3/2006 | Augustine | |

(Continued)

FOREIGN PATENT DOCUMENTS

| | | | | |
|---|---|---|---|---|
| KR | WO 2007073042 A1 * | 6/2007 | ......... | B65D 81/2015 |
| WO | WO 0233404 A2 * | 4/2002 | ......... | G01N 33/146 |

(Continued)

OTHER PUBLICATIONS

Lim Victor et al: 11 Noninvasive Identification of Tainted Corks in Full Intact Wine Bottles: A Low-Pressure Room Temperature Study 11 , American Journal of Enology and Viticulture, American Society for Enology and Viticulture, US, val. 62, No. 3, Sep. 2011 (Sep. 2011), pp. 291-297, XP009171405, ISSN: 0002-9254, DOI: 10.5344/AJEV.2011.10106 [retrieved on May 1, 2011].

(Continued)

*Primary Examiner* — Nguyen Ha
(74) *Attorney, Agent, or Firm* — Thomas | Horstemeyer, LLP

(57) ABSTRACT

In one embodiment, authentication of a beverage is performed by forming an airtight seal with a bottle that contains the beverage, the bottle being sealed with a closure, applying a vacuum to the bottle to draw a sample from the closure that includes traces of the beverage, collecting the sample over time as the vacuum is applied to the closure, and performing testing on the collected sample.

23 Claims, 7 Drawing Sheets

(51) Int. Cl.
*G01N 1/24* (2006.01)
*G01N 30/00* (2006.01)

(56) References Cited

U.S. PATENT DOCUMENTS

| | | | |
|---|---|---|---|
| 9,488,599 B2* | 11/2016 | Augustine | G01N 22/00 |
| 2006/0073295 A1* | 4/2006 | Angermaier | B65D 39/0058 |
| | | | 428/35.7 |
| 2006/0141718 A1 | 6/2006 | Harvey | |
| 2008/0180111 A1* | 7/2008 | Federici | G01N 21/3581 |
| | | | 324/639 |
| 2009/0038374 A1 | 2/2009 | Broz | |
| 2011/0046896 A1 | 2/2011 | Smajlovic | |
| 2011/0184681 A1 | 7/2011 | Augustine et al. | |
| 2012/0037804 A1* | 2/2012 | Federici | G01N 21/3586 |
| | | | 250/341.1 |

FOREIGN PATENT DOCUMENTS

| | | | |
|---|---|---|---|
| WO | 2007141718 | 12/2007 | |
| WO | WO 2011059499 A1 * | 5/2011 | G01N 22/00 |

OTHER PUBLICATIONS

Zoppi U et al: 11 Forensic applications of <14>C bomb-pulse dating 11, Nuclear Instruments & Methods in Physics Research, Section—B:Beam Interactions With Materials and Atoms, Elsevier, Amsterdam, NL, val. 223-224, Aug. 2004 (Aug. 2004), pp. 770-775, XP004525989, ISSN: 0168-583X, DOI: 10.1016/J.NIMB.2004.04.143.

L. Wacker et al: "A versatile gas interface for routine radiocarbon analysis with a gas ion source". Nuclear Instruments and Methods in Physics Research Section B: Beam Interactions With Materials and Atoms. val. 294, Jan. 2013 (Jan. 2013). pp. 315-319. XP055073116, ISSN: 0168-583X, DOI: 10.1016jj.nimb.2012.02.009.

Gerard J Martin et al: "New isotopic criteria for the short-term dating of brandies and spirits". Journal of the Science of Food and Agriculture. val. 77. No. 2. Jun. 1998 (Jun. 1998). pp. 153-160, XP055073078, ISSN: 0022-5142, DOI: 10.1002/(SICI)1097-0010(199806)77:2<153::A ID-JSFA19>3.0.C0;2-3.

International Search Report and Written Opinion for PCT/US2013/032419 dated Aug. 2, 2013.

BevScanTM, Jeffress Engineering Pty Ltd, http://www.jeffress.com.au/products_bs01.htm, accessed Feb. 26, 2013.

Bossew P, Ditto M, Falkner T, Henrich E, Kienzl K, Rappelsberger U. (2001). Contamination of Austrian soil with caesium-137. Journal of Environmental Radioactivity 55: 187-194.

Burchuladze AA, Pagava SV, Povinec P, Togonidze GI, and Usacev S. (1980). Radiocarbon variations with the 11-year solar-cycle during the last century. Nature 287: 320-322.

CALIBomb software, http://calib.qub.ac.uk/ by P.J. Reimer and R.W. Reimer, accessed on Feb. 10, 2013.

Christoph N, Rossmann A, Voerkelius S. (2003). Possibilities and limitations of wine authentication using stable isotope and meteorological data, data banks and statistical tests. Part 1: Wines from Franconia and Lake Constance 1992 to 2001. Mitteilungen Klostemeuburg 53: 23-40.

Cozzolino D, Kwiatkowski MJ, Waters EJ, and Gishen M. (2007). A feasibility study on the use of visible and short wavelengths in the near-infrared region for the non-destructive measurement of wine composition. Analytical and Bioanalytical Chemistry 387: 2289-2295.

DeYoung PA, Hall CC, Mears PJ, Padilla DJ, Sampson R, and Peaslee GF. (2011). Comparison of glass fragments using particle-induced X-ray emission (PIXE) spectrometry. Journal of Forensic Sciences 56(2): 366-371.

Finan T. and Levy A. (2012). Top wine trading company 'filled vintage bottle with alcohol as part of multimillion pound fraud.'

Dailymail, Jun. 15, 2012. http://www.dailymail.co.uk/news/article-2159245/Top-wine-trading-company-filled-vintage-bottles-cheap-alcohol-multimillion-pound-fraud.html, accessed Mar. 5, 2013.

Frank M. (2006). Right Bottle, Wrong Wine. Wine Spectator, Dec. 20, 2006. http://www.winespectator.com/webfeature/show/id/Right-Bottle-Wrong-Wine_3325, accessed Mar. 5, 2013.

Harley SJ, Lim V, Augustine MP. (2012). Application of bivariate statistics to full wine bottle diamagnetic screening data. Talanta 89: 484-489.

Harley SJ, Lim V, Stucky PA, Augustine MP. (2011). Using low frequency full bottle diamagnetic screening to study collectible wine. Talanta 85: 2437-2444.

Hubert Ph, Perrot F, Gaye J, Médina B, Pravikoff MS. (2009). Radioactivity measurements applied to the dating and authentication of old wines. Comptes Rendus Physique 10: 622-629.

Hubert Ph. (2007). From the mass of the neutrino to the dating of wine. Nuclear instruments and methods in Physics Research A 580: 751-755.

Karbowiak T, Gougeon RD, Alinc JB, Brachais L, Debeaufort F, Voilley A, Chassagne D. (2012). Wine oxidation and the role of cork. Critical Reviews in Food Science and Nutrition 50(1): 20-52.

L' Orange R, and Zimen KE. (1968). Scintillation measurement of carbon-14 from nuclear explosions in ethyl alcohol from uncut wines. Naturwissenschaften 55(1): 35-36.

Levin I, and Kromer B. (2004) The tropospheric 14CO2 level in mid latitudes of the Northern Hemisphere. Radiocarbon 46(3): 1261-1272.

Liu L, Cozzolino D, Cynkar WU, Dambergs RG, Janik L, O'Neill BK, Colby CB, and Gishen M. (2008). Preliminary study on the application of visible-near infrared spectroscopy and chemometrics to classify Riesling wines from different countries. Food Chemistry 106: 781-786.

Lopes P, Saucier C, Teissedre PL, Glories Y. (2006). Impact of storage position on oxygen ingress through different closures into wine bottles. Journal of Agricultural Food Chemistry (54) 6741-6746.

Martin GJ, Martin ML, Mabon F, and Michon MJ. (1982). Identification of the origin of natural alcohols by natural abundance hydrogen-2 nuclear magnetic resonance. Analytical Chemistry 54(13): 2380-2382.

Martin GJ, Thibault J, Bertrand MJ. (1995). Spatial and temporal dependence of the 13C and 14C isotopes of wine ethanols. Radiocarbon 37: 943-954.

Meltzer PD. (2013). Worldwide wine auction revenues fall in 2012. Wine Spectator, Jan. 15, 2013. http://www.winespectator.com/webfeature/show/id/47905, accessed Mar. 5, 2013.

Moore M. (2011). Empty wine bottles sell for £300 in China. The Telegraph, Jan. 7, 2011. http://www.telegraph.co.uk/foodanddrink/wine/8246212/Empty-wine-bottles-sell-for-300-in-China.html, accessed Mar. 5, 2013.

Pierson D. (2012). Pricey counterfeit labels proliferate as China wine market booms. Los Angeles Times, Jan. 14, 2012. http://articles.latimes.com/2012/jan/14/business/la-fi-china-counterfeit-wine-20120115, accessed Feb. 28, 2013.

Ram V. (2009). Wine Futures. Forbes.com, Jul. 13, 2009. http://www.forbes.com/2009/07/13/livex-wines-futures-markets-equity-entrepreneur.html, accessed Mar. 5, 2013.

Reimer PJ, Baillie MGL, Bard E, Bayliss A, Beck JW, Blackwell PG, Ramsey CB, Buck CE, Burr GS, Edwards RL, Friedrich M, Grootes PM, Guilderson TP, Hajdas I, Heaton TJ, Hogg AG, Hughen KA, Kaiser KF, Kromer B, McCormac FG, Manning SW, Reimer RW, Richards DA, Southon JR, Talamo S, Turney CSM, van der Plicht J, and Weyhenmeye CE. (2009) IntCal09 and Marine09 radiocarbon age calibration curves, 0-50,000 years cal BP. Radiocarbon 51: 1111-1150.

Reimer PJ, Brown TA, Reimer RW. (2004). Discussion: Reporting and calibration of post-bomb 14C data. Radiocarbon 46: 1299-1304.

Rossmann A. (2001). Determination of stable isotope ratios in food analysis. Food Reviews International 17(3): 347-381.

Santos GM, Moore RB, Southon JR, Griffin S, Hinger E, Zhang D. (2007). AMS C-14 sample preparation at the KCCAMS/UCI facility: Status report and performance of small samples. Radiocarbon 49(2): 255-269.

(56) References Cited

OTHER PUBLICATIONS

Southon J, Santos GM. (2007). Life with MC-SNICS. Part II: Further ion source development at the Keck carbon cycle AMS facility. Nuclear Instruments & Methods in Physics Research Section B 259(1): 88-93.
Steinberger M. (2012). A Vintage Crime. Vanity Fair, Jul. 2012. http://www.vanityfair.com/culture/2012/07/wine-fraud-rudy-kumiawan-vintage-burgundies, accessed Mar. 5, 2013.
Stuiver M, Polach HA. (1977). Discussion: Reporting of 14C data. Radiocarbon 19(3): 355-363.
The Economist. (2011). Château Lafake, Jun. 16, 2011. http://www.economist.com/node/18836894, accessed Mar. 5, 2013.
Weekley AJ, Bruins P, Sisto M, Augustine MP. (2003). Using NMR to study full intact wine bottles. Journal of Magnetic Resonance 161: 91-98.
Weekley AJ, Bruins, P, and Augustine, MP. (2002). Nondestructive method of determining acetic acid spoilage in an unopened bottle of wine. American Journal of Enology and Viticulture 53(4): 318-321.

\* cited by examiner

SYSTEM AND METHOD FOR NON-INVASIVELY AND NON-DESTRUCTIVELY AUTHENTICATING BOTTLED BEVERAGES

CROSS-REFERENCE TO RELATED APPLICATION

This application is the 35 U.S.C. §371 national stage of, and claims priority to and the benefit of, PCT application PCT/US2013/032419, filed Mar. 15, 2013, herein incorporated by reference in their entirety.

BACKGROUND

In 2012, worldwide auction sales of fine and rare wine totaled $389 million. While the average price per lot in the U.S. was $2,792, large sums of money were spent on unique or rare bottles of wine from prestigious Château's for exceptional years. For example, in 2012 at an Acker Merrall & Condit's auction in Hong Kong, a 12-bottle case of the Château Mouton-Rothschild 1945 sold for a staggering $214,256. That same year at a Christie's auction in London, a 12-bottle case of Château Cheval-Blanc 1947 fetched a price of $203,918, and at a Sotheby's auction in New York a single bottle of the famed dessert wine Château d'Yquem 1892 was sold for $55,125. In addition, fine and rare wines have changed from just rarefied collectables to investment vehicles for high net worth individuals.

While the amount of money spent on fine and rare wines in 2012 was substantial, it actually represents a decrease of 19% compared to sales figures in 2011, and this was the first decrease since 2009. Although there are many factors that contributed to this decline, wine fraud has had a significant effect on wine prices. Specifically, wine fraud has cast a shadow of suspicion over the fine and rare wine market that has had a chilling effect on the purchasing of such wine. Although wine fraud is not new, the stratospheric surge in the prices of fine and rare wines in the last decades has provided an increased incentive for unscrupulous individuals to try and pass off counterfeits as the authentic product in order to make a quick and substantial profit.

The most certain way to confirm the authenticity of a wine is to open the bottle in which it is stored and test the wine to make a determination as to whether or not it is genuine. Unfortunately, such a procedure renders the wine unsalable and, therefore, worthless. Accordingly, this method is both invasive and destructive.

From the above discussion it can be appreciated that it would be desirable to have a non-invasive and non-destructive way to authenticate bottled beverages, such as wine, to combat fraud and increase consumer confidence in the authenticity of such beverages.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a non-invasive and non-destructive way to authenticate bottled beverages, such as wine, to combat fraud and increase consumer confidence in the authenticity of such beverages. Described herein are systems and methods suited for this purpose. The systems and methods are used to extract a fractional sample of the beverage through a porous closure used to seal the bottle in which the beverage is contained without opening the bottle, damaging the closure, or damaging the beverage. In some embodiments, the beverage sample is extracted by applying a vacuum to the bottleneck and closure for an extended period of time. Once extracted, the sample can be tested. In some embodiments, the sample is tested by performing radiocarbon dating and/or evaluating its stable isotope ratios.

In the following disclosure, various specific embodiments are described. It is to be understood that those embodiments are example implementations of the disclosed inventions and that alternative embodiments are possible. All such embodiments are intended to fall within the scope of this disclosure.

As mentioned above, the inventive systems and methods can be used to extract and analyze a fractional sample of wine from its bottle through the bottle closure. As will be apparent from the discussion that follows, verification of the vintage and quality of wine is possible without opening the bottle or compromising its closure. The systems and methods therefore represent a significant advance over previous techniques that require opening the bottle or passing a needle through its closure.

By collecting the samples under vacuum conditions (e.g., approximately 0.5 Torr to $10^{-3}$ Torr), absorbed gases and, more importantly, absorbed liquids are allowed to vaporize and can be measured directly or collected cryogenically for later analysis. One goal is to extract ethanol for isotopic analysis, such as $^{14}C$ dating. The advantage of $^{14}C$ dating over other dating methods is that single bottles of wine from any origin can be dated without the need of a verified reference sample. This is because a well-established record exists of the $^{14}$C level before and during the atomic age. For most wines, the so-called radiocarbon bomb peak can be used for wine dating. In addition, the disclosed systems and methods can be used to study the stable isotope ratios (e.g., $\delta D$, $\delta^{13}C$, $\delta^{18}O$) on wine from closed bottles. Furthermore, chemical analysis can be performed on the extracted samples to test for spoilage or fault markers, such as acetic acid, acetaldehyde, 4-ethylphenol, and geosmin.

Figure 1:
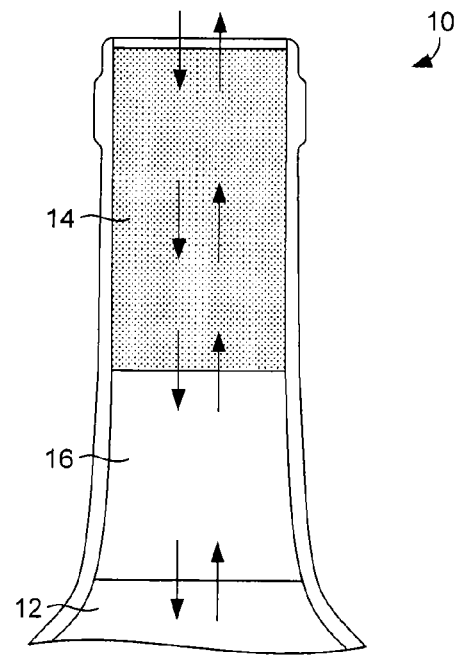
FIG. 1 is a schematic diagram of a sealed wine bottle that illustrates the transport of vapors and gasses through a closure of the bottle.

FIG. 1 shows a conventional wine bottle 10 that contains wine 12 and is sealed with a porous closure 14. In the typical case, the closure 14 is not entirely vacuum-tight and enables some exchange of gasses and vapors from the ullage 16, i.e., the headspace between the liquid and the closure. Limited exchange with atmospheric air and oxygen within the ullage 16 is desired and plays a role in the maturation of wine. For practical and traditional reasons, the most widely used material for closures is cork made from the bark of the cork oak tree (Quercus suber L.). Because of this material's porosity, cork closures take up and store fractions of water, ethanol, and other components of wine over time. The basic principle of the wine authentication and spoilage testing described herein is the extraction of these wine "traces" from the cork closure.

FIG. 1 illustrates the permeation of wine components from the liquid or gas phase to the outside of the bottle 10. If the wine 12 is not in direct contact with the closure 14, the phase transition from liquid wine to wine vapor can be described by Raoult's law for the principal components (water and ethanol) and by Henry's law for analytes of low concentration. Permeation through the closure 14 includes the processes of sorption of the analytes into the closure material following Henry's law, diffusion through the material, and finally desorption on the outside of the material, again described by Henry's law. Henry's law is applicable to both liquid and solid phases because absorption into the closure 14 is similar to the solubility in a liquid. For a system in equilibrium, Henry's law describes the partial pressure $p_{part}$ of a species over a solution with concentration C of that species:

$$p_{part} = k_H \cdot C \text{ or } C = \frac{p_{part}}{k_H} \quad \text{[Equation 1]}$$

where $k_H$ is the empirically-determined Henry's law constant.

Once the species of interest is sorbed in the porous closure, diffusion processes will take place. Laws such as Knudsen's law (which states that the mean free path of the diffusing species is much larger than the pore the species it is diffusing through) can be used to describe the diffusion of relatively dilute gases. In a general consideration, Fick's first law can be used to describe the diffusive flux J (kg m$^{-2}$ s$^{-1}$) of a species in an isotropic medium with a one-dimensional concentration gradient when the system is in steady state and the diffusion coefficient D (m$^2$ s$^{-1}$) is independent of the concentration of the species of interest:

$$J = -D \cdot \frac{dC}{dx} \quad \text{[Equation 2]}$$

where C is the concentration (kg m$^{-3}$) and x the distance (m).

The permeability P (kg m$^{-1}$ s$^{-1}$ Pa$^{-1}$) is then given by:

$$P = D \cdot S \quad \text{[Equation 3]}$$

where S (kg m$^{-3}$ Pa$^{-1}$) is the sorption coefficient and is equal to the Henry's law constant $k_H$ in the case of a linear sorption isotherm.

Diffusive flux and permeation depend on many factors such as the mass of the molecule of interest, its diameter, its sorption isotherm with the sorbent (in the simplest, linear case a Henry's law constant, otherwise a more complex function of pressure or concentration), its concentration or pressure, the temperature, as well as the porosity and tortuosity of the diffusion medium.

In addition to diffusion processes and their different regimes, transport mechanisms of liquids such as capillarity (depending on the adhesion of the liquid in the pore and the pore diameter) or Darcy's law (a laminar flow through porous media) may be effective to a limited extent in the macro pores of a cork closure in wine.

It is important to note that the permeation through cork occurs at very low rates. The only process that can be significantly accelerated from outside the bottle is the desorption of compounds from the cork. Therefore, a vacuum is applied to the closure in order to achieve reasonably short sampling times and sufficient sample sizes for testing. Under vacuum, wine traces will evaporate and are therefore efficiently removed from the closure. Vapor pressure and sorption properties of the species of interest as well as the closure structure determine the outgassing rates of different species. However, the vacuum will only affect the top of the closure where lowered pressures are effective to desorb wine traces.

Figure 2:
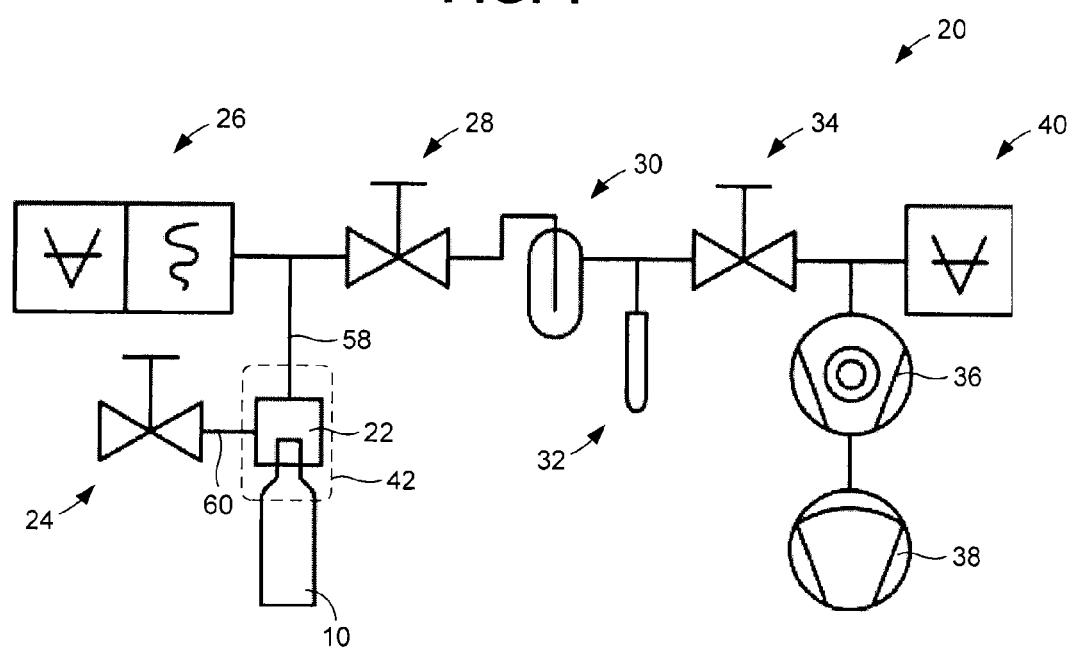
FIG. 2 is a block diagram of an embodiment of a system for non-invasively and non-destructively authenticating bottled beverages.

FIG. 2 illustrates an embodiment of a system 20 for non-invasively and non-destructively authenticating bottled beverages. As shown in that figure, the system 20 generally includes a vacuum line that can be used to form a relatively strong vacuum over the top end of the wine bottle 10. In some embodiments, a vacuum of $1 \times 10^{-4}$ Torr or stronger can be produced by the vacuum line. As is also shown in FIG. 2, the vacuum line comprises multiple fluid lines (e.g., tubes) and valves, some of which are described below. In some embodiments, the lines and valves have either a ¼ or ½ inch inner diameter in order to allow sufficient pumping over the wine samples and thus fast trapping of low-vapor pressure substances, such as water and ethanol.

Figure 3:
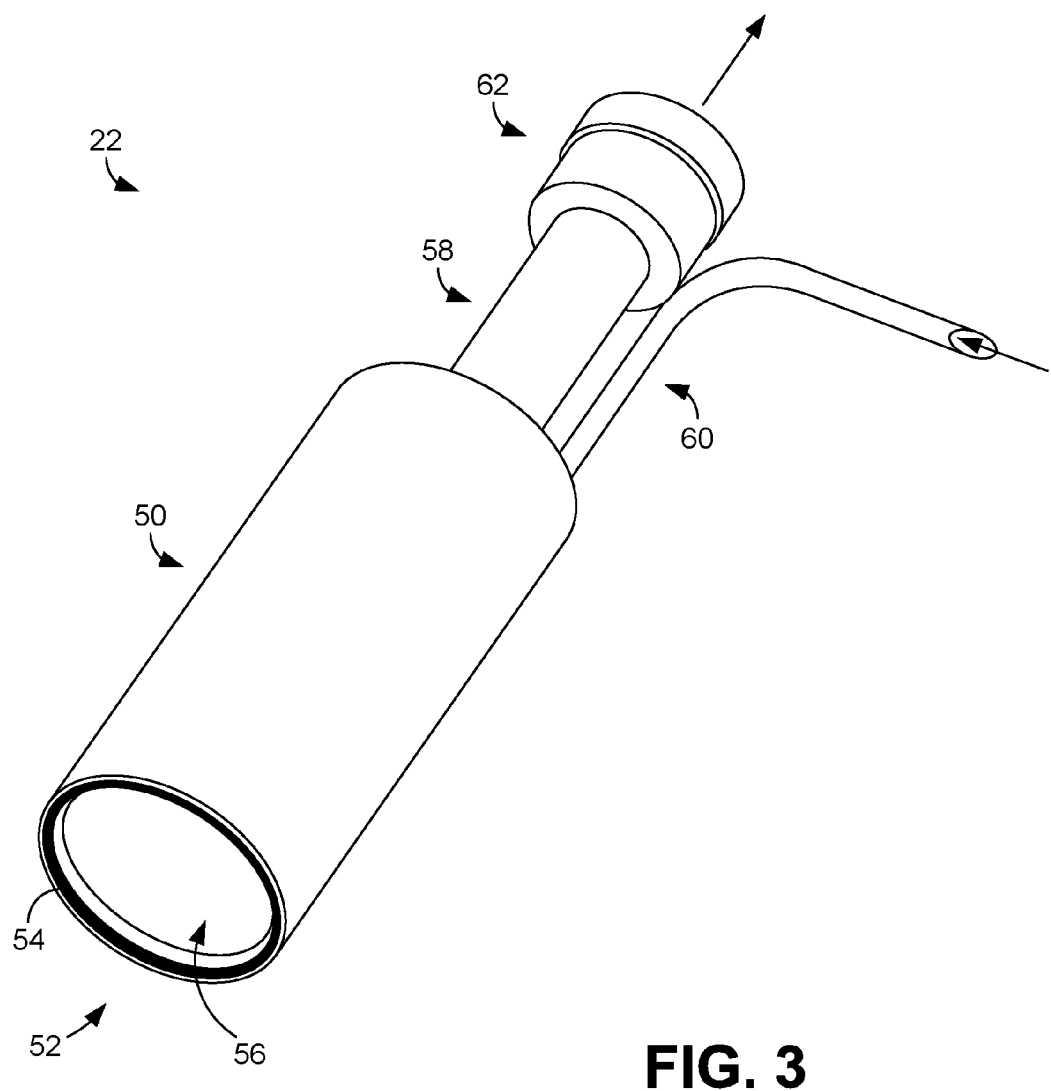
FIG. 3 is a perspective view of an embodiment of a bottle coupling device of the system of FIG. 2.
Figure 4:
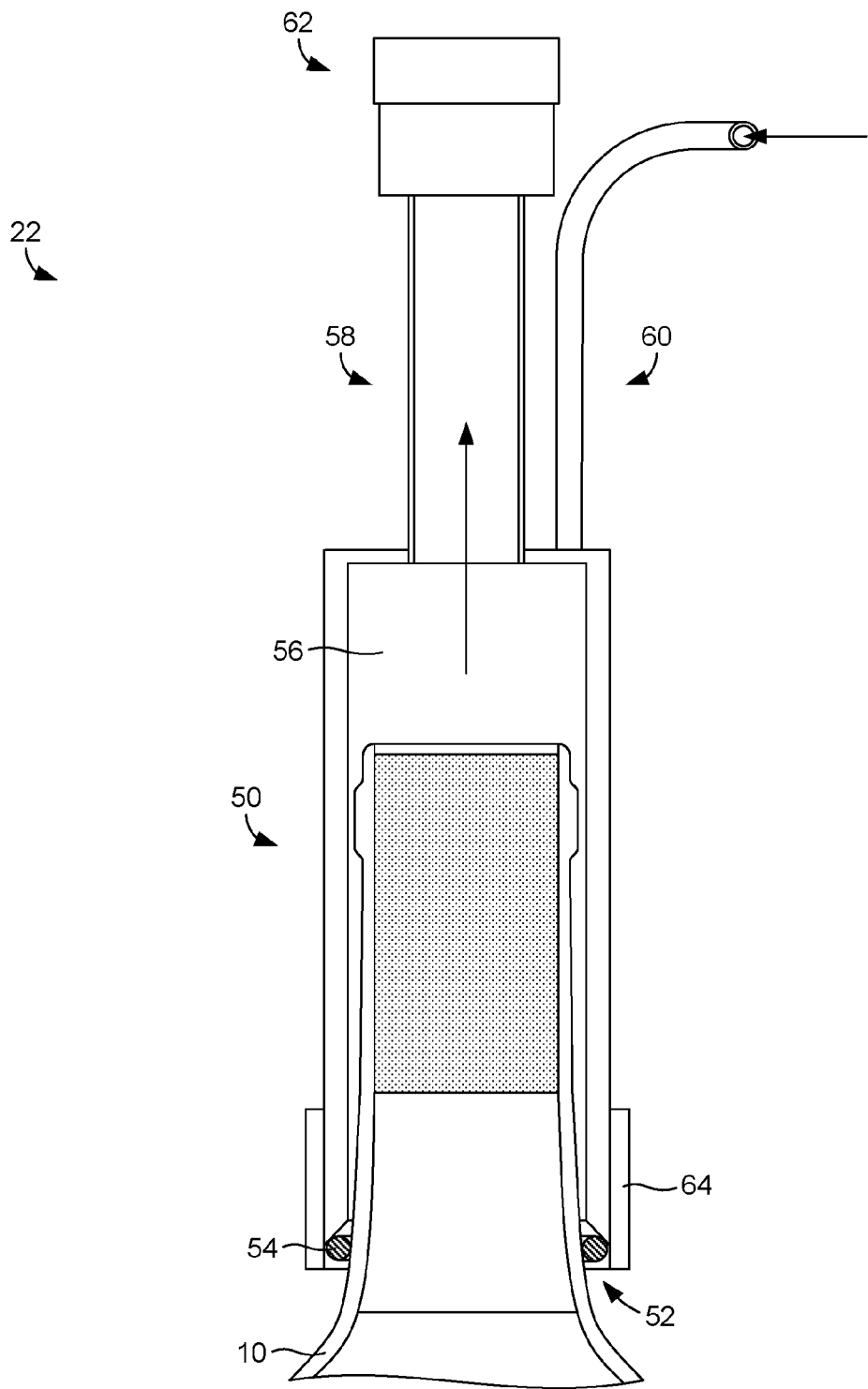
FIG. 4 is a partial side cut-away view of the bottle coupling device of FIG. 2 shown applied to a wine bottle.

With further reference to FIG. 2, the vacuum line couples to the wine bottle 10 using a bottle coupling device 22 that forms an air-tight seal with the top of the bottle. An example embodiment for the bottle coupling device 22 is illustrated in FIGS. 3 and 4. As shown in those figures, the bottle coupling device 22 generally comprises a hollow cylindrical body 50 that is adapted to fit around the neck of the wine bottle 10. In embodiments intended for standard wine bottles, the body 50 can have an inner diameter of approximately 1¼ inches and is made of stainless steel. Of course, other sizes are possible for bottles of other sizes. As shown in FIG. 4, an opening 52 is provided at the bottom end of the body 50 through which the top of the wine bottle 10 can pass. To ensure that an air-tight seal is formed between the bottle coupling device 22 and the bottle 10, a resilient sealing member 54, such as a rubber O-ring, is provided at the body opening 52. In some embodiments, small amounts of high-vacuum grease can be provided on the sealing member 54 to ensure optimal sealing.

With further reference to FIG. 4, the body 50 forms a cylindrical interior space 56 in which the top of the bottle 10 can be positioned. In fluid communication with the interior space 56 and extending from a top end of the body 50 are two fluid lines, including a sample line 58 and a vent line 60. The sample line 58 is used to collect wine samples from the bottle 10. In some embodiments, the sample line 58 is a stainless steel cylindrical tube having an inner diameter of approximately ½ inch. Mounted to a top end of the sample line 58 is a coupler 62 that is used to connect the bottle coupling device 22 to the remainder of the system 20. In some embodiments, the coupler comprises a ½ inch Ultra-Torr port (Swagelok, USA).

The vent line 60 is used to vent the interior space 56 of the bottle coupling device 22 and, in some embodiments, to flush the space with an inert gas. In some embodiments, the vent line 60 comprises an ⅛ inch stainless steel capillary tube.

With further reference to FIG. 4, the bottle coupling device 22 can also include a collar 64 that helps retain the sealing member 54.

Irrespective of its particular design, the bottle coupling device 22 is configured to minimize dead volume and, more importantly, to ensure small leak rates, which affect both yield and measurement accuracy of subsequent analysis.

With reference back to FIG. 2, in fluid communication with the vent line 60 of the bottle coupling device 22 is a venting valve 24. Like the vent line 60, the venting valve 24 is used to vent the interior space 56 and further can be used to flush the space. In some embodiments, the venting valve 24 is a plug valve.

In fluid communication with the sample line 58 is a first pressure sensor 26 that can be used to monitor the pressure of the interior space 56. In some embodiments, the pressure sensor 26 comprises a Pirani pressure sensor. Also in fluid communication with the sample line 58 is a first shut-off valve 28 that can be used to prevent or enable fluid communication between the bottle coupling device 22 and the remainder of the vacuum line. In some embodiments, the shut-off valve 28 is a plug valve.

The shut-off valve 28 is in fluid communication with a cryotrap 30 that is used to trap and freeze collected samples. In some embodiments, the cryotrap 30 comprises ¼ inch bellows tubing cooled with liquid nitrogen. In fluid communication with the cryotrap 30 in the illustrated embodiment is a prebaked quartz glass tube 32. In some embodiments, the tube 32 contains approximately 60-70 mg of cupric oxide (CuO). After trapping, the sample contained in the bellows (mostly water and ethanol) can be cryogenically transferred to the glass tube 32 and the tube is closed, for example, with an oxyacetylene torch, to form an airtight ampoule.

In fluid communication with the glass tube 32 is a second shut-off valve 34 that is also in fluid communication with one or more vacuum pumps. In the illustrated embodiment, the pumps include a turbomolecular pump 36 (HiPace 80, Pfeiffer Vacuum, Germany) and a diaphragm pump 38 (MVP 040-2, Pfeiffer Vacuum, Germany) that are connected in series. The pressure levels created by the pumps are measured by a second pressure sensor 40, which can also be a Pirani pressure sensor.

During the sampling period, analog signals from the first pressure sensor 26 are converted to digital signals that are recorded, for example, with a LabView™ program. Because the integrated pressure signal from the pressure sensor 26 is proportional to the number of molecules that are extracted from the cork closure, the time and pressure information indicates the sampling time needed to obtain a sample of sufficient size for testing. Under the assumption of constant temperature over the sampling time as well as constant pumping speed of the cryotrap and the turbomolecular pump over the observed pressure range, it can be shown that:

$$\int_{t_o}^{t_1} p\, dt \propto n \qquad \text{[Equation 4]}$$

where p is pressure (Pa) and n the number of moles sampled. The proportionality factor in this equation is the pumping speed and the conductance of the system. Therefore, every vacuum line will have a specific proportionality factor depending on the diameter, length, and geometry of the tubing, as well as the cryotrap and pump properties. This proportionality factor can be determined empirically from the slope of the linear regression of pressure integrals and carbon amounts (see FIG. 5).

The sample amounts required for analysis vary by orders of magnitude depending on the analyte of interest and the measurement method. In the case of $^{14}C$ analysis, tens of micrograms to about 1 milligram of carbon are desirable for radiocarbon dating using accelerator mass spectrometry (AMS) for the precise determination of sample age. Typically hundreds of nanograms of sample are required for stable isotope studies, while the sample size requirements for the detection of spoilage markers with conventional mass spectrometry vary with the analyte in question.

Described next is an example method for obtaining a wine sample using the apparatus described above in relation to FIG. 2. It is noted that not all of the steps of the example method must be performed in all cases. The wine can be maintained at the desired storage temperature (e.g., 13 to 15° C.) over the entire sampling time and no cooling or heating of the wine occurs from the sampling.

First, a blind flange (not shown) is inserted into the bottle coupling device 22 to seal the opening 52 of the device from the atmosphere. The vacuum line of the system 20 can then pumped down to less than $10^{-4}$ Torr. Next, the first shut-off valve 28 is closed and the bottle coupling device 22 is vented with an inert gas, such as argon, or nitrogen that is delivered to the interior space 56 of the device via the vent line 60 and the venting valve 24.

The top and neck of the bottle 10 to be analyzed are cleaned, for example, using a laboratory wipe, to ensure a good seal with the bottle coupling device 22 and can be blown with compressed air to remove any dust or lint. A plastic bag 42 (FIG. 2) is then taped around the bottle 10 and the bottle coupling device 22 and the bag is inflated with the inert gas. Special care is taken to avoid contamination from atmospheric $CO_2$ because sample-to-sample variations in leak rates may influence samples differently. The blind flange is then removed from the bottle coupling device 22 and the bottle 10 is inserted through the device opening 52. The venting valve 24 is next opened in order to flush the bottle coupling device 22 with the inert gas to remove any atmospheric air.

At this point, data acquisition from the pressure sensor 26 is initiated and the venting valve 24 is closed. Next, the first shut-off valve 28 is opened and the bottle coupling device 22 develops an airtight seal with the bottle 10. When a vacuum of less than $5 \times 10^{-1}$ Torr or a stable pressure is reached, the first shut-off valve 28 is closed. The downstream end of the vacuum line is then pumped to a vacuum of approximately $10^{-3}$ Torr and the cryotrap 30 is cooled with liquid nitrogen.

Next, the first shut-off valve 28 is again opened and the wine is sampled for an extended period of time while the closure is under vacuum and continuous pumping. In some embodiments, the wine is sampled for approximately 30 to 120 minutes at a pressure of approximately 0.5 to $10^{-3}$ Torr. The duration used may depend upon the individual wine bottle under study and the quality of closure. Because the pressure applied to the closure is measured during sampling, the quality of the closure can also be determined during the testing. Specifically, relatively low pressures (e.g., 0.5 Torr) will be reached nearly immediately upon applying the vacuum closure when the closure is of good quality. When the closure is of bad quality (i.e., leaky), however, lower pressures will be more difficult to achieve. Leaky closures will exhibit high oxygen transmission rates (OTRs) that can lead to oxidation damage to the wine. Simultaneous to cryotrapping of ethanol and water, a portion of the sampled gases can be measured with a conventional mass spectrometer (e.g., MS/MS) to test for tracers of wine spoilage or wine fault (e.g., acetic acid, acetaldehyde, 4-ethylphenol, and geosmin).

After sampling, the cryotrap 30 and the glass tube 32 are closed off from the bottle coupling device 22 and the vacuum line by closing both shut-off valves 28, 34. The liquid nitrogen is moved from the cryotrap 30 to the glass tube 32 and the cryotrap is heated (e.g., to ~100° C.) to volatilize the water and ethanol and to freeze them in the glass tube. The second shut-off valve 34 is then opened to pump away any residual gas and the tube 32 is sealed off, for example, using an oxyacetylene torch. The bottle coupling device 22 can next be bled up to atmospheric pressure with the inert gas. If the closure 14 is to be rehydrated, the gas can be humidified with clean water.

After this sampling procedure, the blind flange is re-inserted into the bottle coupling device 22 and the vacuum line is pumped down in order to minimize the risk of cross-contamination. Then, the shut-off valves 28, 34 are closed to swap out the glass tube 32 with a new glass tube. As soon as the vacuum is less than $10^{-4}$ Torr, the next wine bottle can be sampled.

The above-described sampling procedure was applied to reference solutions in order to assess the sources of carbon contamination (other than the sample ethanol). A 1% volumetric solution of methanol (Fisher Scientific, USA) and a 4% volumetric solution of Three Wishes Merlot (no vintage, purchased in summer 2012, Whole Foods, USA) were made up with deionized water. The methanol was $^{14}$C-depleted (radiocarbon dead, from fossil sources) while the Three Wishes Merlot had a "modern" radiocarbon value similar to the current atmospheric $^{14}$C value.

In order to avoid possible cross-contamination of the wine bottles, the stainless steel parts of the system 20 can be heated (e.g., to 200° C.) with a heat gun under vacuum. The bottle coupling device 22 can be cleaned by removing it from the system 20 and mechanically cleaning off any macroscopic contaminants (e.g., vacuum grease, dust) with a laboratory wipe. Further cleaning can be achieved by immersion and sonication in a commercially-available cleaning/sanitizing solution containing no bleach or other halogen compounds.

The ampoule containing the sample and CuO can be stored indefinitely and conveniently transported. For further sample preparation, the ampoules can be heated up to 900° C. for 3 hours in order to oxidize all organics to $CO_2$. After oxidation, the tubes can be scored and cracked in a vacuum line. The released $CO_2$ is transferred to a graphite reactor, which reduces the $CO_2$ to elemental carbon (filamentous graphite) at 450 to 550° C. and under the presence of stoichiometric amounts of hydrogen and approximately 5 mg of iron powder (-325 mesh, Alfa Aesar, USA) as a catalyst. The graphite/iron mixture is then pressed into an aluminum holder, which is used as a cathode in the negative sputter ion source of an accelerator mass spectrometer, and radiocarbon dated.

After measurement, radiocarbon values can be corrected. Sample $^{14}C/^{12}C$ ratios are normalized to those of a radiocarbon standard using measured $^{14}C/^{12}C$ ratios of the NIST OX-I reference material and are corrected for isotopic fractionation using $^{13}C/^{12}C$ ratios ($\delta^{13}C$ values) measured for every sample. The obtained dimensionless number is then termed $F^{14}C$ and is used together with its uncertainty to calculate the corresponding calendar year of the wine.

Figure 7A:
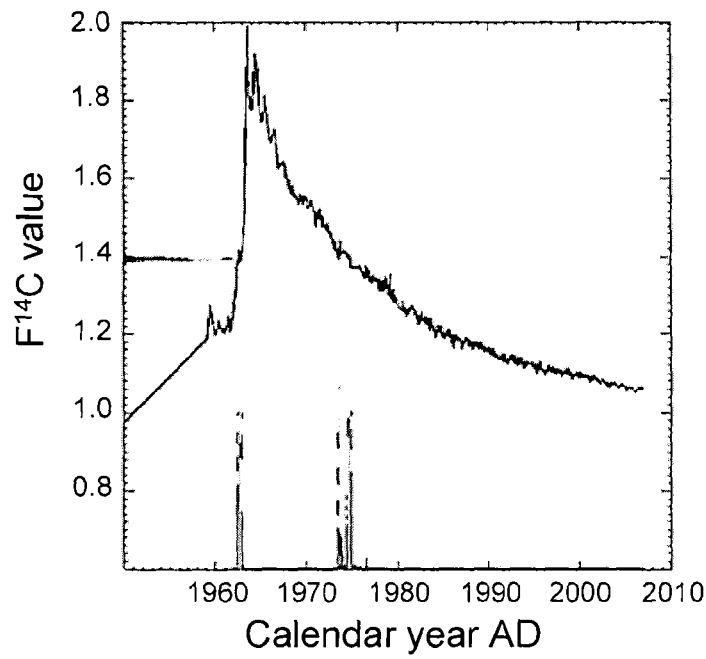
FIGS. 7A and 7B are graphs of the bomb-peak calibration curve with $F^{14}C$ values (y-axis) and calibrated calendar years (x-axis) for a 1962 Château Lafite-Rothschild and a 1991 Stag's Leap Cabernet Sauvignon, respectively. Both $1\sigma$ intervals (light) and $2\sigma$ intervals (dark) are identified in the graphs.
Figure 7B:
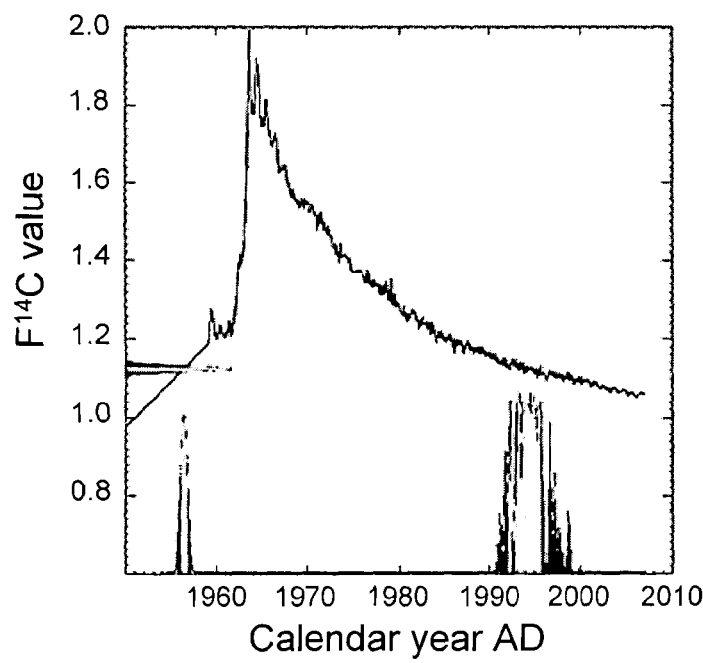

For age ranges from 1950 to the present, this is can be accomplished with the bomb peak calibration curve and the software CALIBomb by P. J. Reimer and R. W. Reimer. The software uses several empirical calibration data sets depending on the geographic origin of the wine. All of 14 radiocarbon samples analyzed in a proof of concept study described below were calibrated with the calibration curve based on the mid-latitude northern hemisphere data from Levin and Kromer (2004) between the years 1959 and 2003. FIGS. 7A and 7B show two calibration graphs obtained after calibration with CALIBomb. The y-axis shows the $F^{14}C$ value as a normal distribution with the 1σ (light) and the 2σ interval (dark). The Gaussian curve of the $F^{14}C$ value is then convoluted with the calibration curve to give a probability distribution for the calendar year of the sample, which is plotted on the x-axis. If the measured wine sample has a non-zero probability at the year on the wine label, the wine can be considered authentic.

In the proof of concept study, wine bottles from 1962 to 1991 were obtained from a private collection and sampled using the above-described system and method. All bottles were in optimal condition and did not show any sign of abnormal cork leakage or damage. The results of the study are described below.

Figure 6:
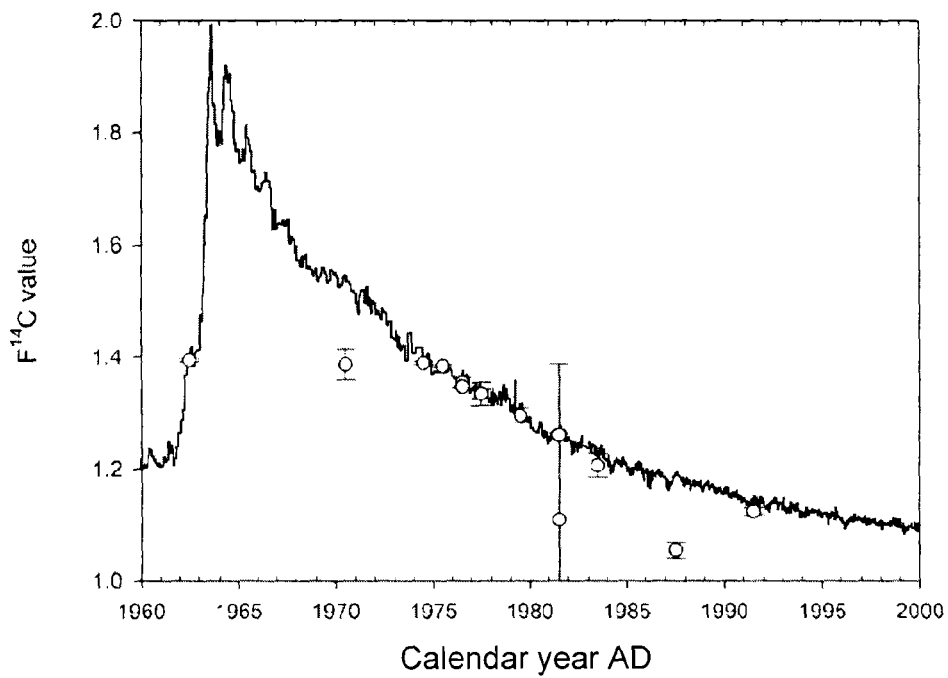
FIG. 6 is graph of the bomb-peak calibration curve and data from 14 analyzed wine bottles (identified with circles). Error bars indicate the uncertainties of the $^{14}C$ values after all background corrections.

All 14 wine bottles were sampled with the vacuum line described in relation to FIG. 2. An overview of the data is given in Table 1. Two examples of calibrated radiocarbon values are shown in FIGS. 7A and 7B for illustration of the calibration precision depending on sample vintage and amounts. In addition, the measured radiocarbon dates of the sampled wines are plotted on the bomb peak calibration curve in FIG. 6.

TABLE 1

| | | | | | | | | |
|---|---|---|---|---|---|---|---|---|
| Compiled Sample Data | | | | | | | | |
| Year | Wine name | Region | Country | Sampling time | Extracted carbon (μg) | $F^{14}C$ | Error | Conformity |
| 1977 | Robert Mondavi Cabernet Sauvignon (Reserve) | Napa Valley | USA | 2 h | 138 | 1.3344 | 0.0085 | Yes |

TABLE 1-continued

Compiled Sample Data

| Year | Wine name | Region | Country | Sampling time | Extracted carbon (μg) | $F^{14}C$ | Error | Conformity |
|---|---|---|---|---|---|---|---|---|
| 1983 | Stag's Leap Wine Cellars Cabernet Sauvignon | Napa Valley | USA | 2 h | 56 | 1.2060 | 0.0209 | Yes |
| 1981 | Robert Mondavi Cabernet Sauvignon | Napa Valley | USA | 3 h | 8 | 1.1095 | 0.2784 | Ambiguous |
| 1987 | Stag's Leap Wine Cellars Cabernet Sauvignon SLV | Napa Valley | USA | 2 h | 25 | 1.0548 | 0.0136 | No |
| 1974 | Sebastiani Cabernet Sauvignon | Sonoma Valley | USA | 2 h | 178 | 1.3889 | 0.0029 | Yes |
| 1981 | Mayacamas Chardonnay | Napa Valley | USA | 1 h | >1'400 | 1.2601 | 0.0022 | Yes |
| 1976 | Mayacamas Cabernet Sauvignon | Napa Valley | USA | 2 h | 54 | 1.3541 | 0.0089 | Yes |
| 1977 | Robert Mondavi Cabernet Sauvignon (Reserve) | Napa Valley | USA | 2 h | 23 | 1.337 | 0.0209 | Yes |
| 1970 | Château Giscours Margaux | Bordeaux | France | 2 h | 19 | 1.3866 | 0.0278 | No |
| 1991 | Stag's Leap Wine Cellars Cabernet Sauvignon FAY | Napa Valley | USA | 2 h | 54 | 1.1243 | 0.0066 | Yes |
| 1975 | Robert Mondavi Cabernet Sauvignon | Napa Valley | USA | 30 min | 907 | 1.3839 | 0.0024 | Yes |
| 1979 | Robert Mondavi Cabernet Sauvignon | Napa Valley | USA | 2 h | 33 | 1.2950 | 0.0135 | Yes |
| 1976 | Mayacamas Cabernet Sauvignon | Napa Valley | USA | 2 h | 83 | 1.3473 | 0.0024 | Yes |
| 1962 | Château Lafite-Rothschild | Bordeaux | France | 30 min | >1'230 | 1.3944 | 0.0026 | Yes |

Calibrated dates of 12 samples overlap with their expected vintages according to CALIBomb, thus verifying the correct age of those wines. Thus, the disclosed non-invasive, non-destructive method for the authentication of the contents of wine bottles has been proven to work successfully. However, two radiocarbon dates (1970 Château Giscours Margaux and 1987 Stag's Leap Wine Cellars Cabernet Sauvignon SLV) showed $^{14}C$ values that were too low for the corresponding vintages. The reason why these particular wine bottles did not yield the correct radiocarbon values is unknown but it could be due to small sample sizes or contamination. In addition, one bottle of wine (1981 Robert Mondavi Cabernet Sauvignon) had a large uncertainty due to its small sample size (8 μg of carbon). Its conformity with the vintage is thus ambiguous as it spans several decades in calendar years.

Figure 5:
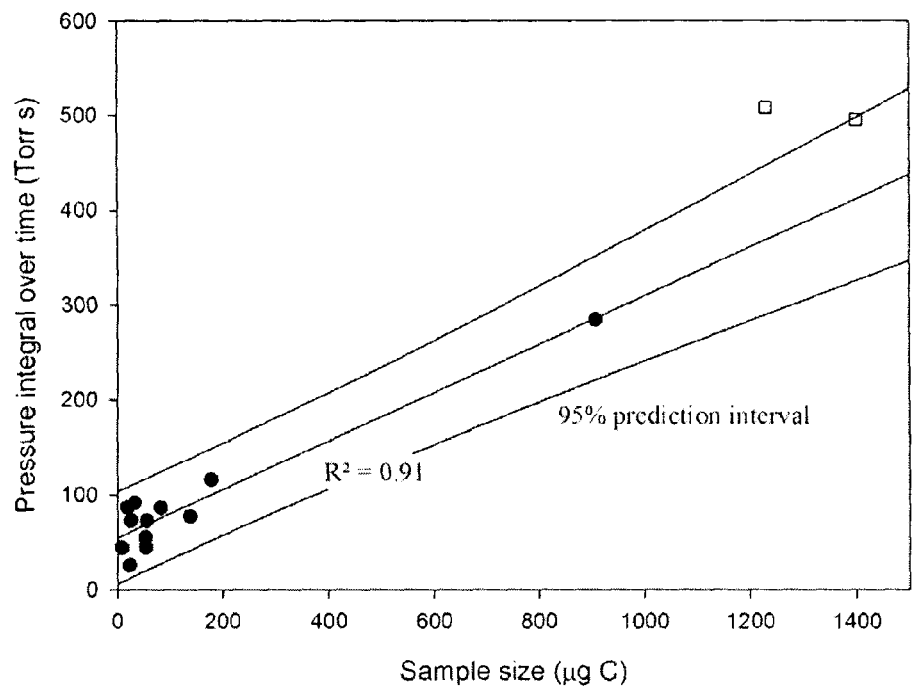
FIG. 5 is a graph that correlates time-integrated pressure measurements with carbon amounts extracted from wine bottles during testing. Squares identify two samples that were too large for full combustion and had to be partially pumped away before their carbon content was measured.

All of the sampling pressure curves were integrated over time and the integrals were plotted against the carbon amounts obtained manometrically from the graphitization reactors (FIG. 5). The $R^2$ value of 0.91 shows a good correlation between sample pressure and carbon amounts obtained, which demonstrates the suitability of pressure measurements for the determination of the sampling time. It should be noted, however, that this correlation is significantly lower in small samples. This is probably due to differences in the relative proportions of wine fluids and absorbed atmospheric water, which will have much more effect when the contribution from inside the bottle (and hence the ethanol sample size) is low.

Processing of standard and radiocarbon-dead materials through portions of the procedure revealed the following carbon analytical blanks: The graphitization, sample pressing, and measurement of the samples added 0.1 μg of radiocarbon-dead carbon and 0.4 to 0.5 μg of modern carbon. An additional 0.3 to 0.8 μg of radiocarbon-dead carbon and 0.2 to 0.5 μg of modern carbon were identified as originating from the vacuum line when sampling for 30 minutes. If the sampling period was extended to 120 minutes, an additional 0.2 to 0.4 μg of radiocarbon-dead carbon and 0.2 to 0.4 μg modern carbon were added to the blanks from the graphitization and the 30 minute sampling. This amounts to a total carbon contamination of 1.4 to 2.7 μg in a 2-hour sample. Implications of these carbon blank levels on the wine age determinations are discussed below.

In order to obtain a precise and accurate radiocarbon value, sample sizes should be relatively large and carbon contamination should be reduced. The reason for the ambiguous dating of the 1981 Robert Mondavi Cabernet Sauvignon (8 μg carbon) is its small size compared to the relatively large contribution from non-sample carbon. The uncertainties in the applied background corrections increase the overall uncertainty of the $F^{14}C$ value considerably, which in turn affects the broadness of the age probability distribution. With the disclosed wine extraction method, there is little room for increased sample sizes as the amounts are limited by the extractable ethanol in the cork. A change in the setup of the vacuum line or a modification of the bottle coupling device 22 may lead to minor improvements but, more importantly, the carbon contamination during sampling should be reduced. This could be done with a vacuum line setup that only relies on stainless steel fittings, abandoning the use of vacuum grease, and more rigorous leak control. Moreover, atmospheric $CO_2$ or volatile organic carbons (VOCs) in the cork are likely contaminants that cannot be separated from the targeted ethanol other than by pumping them away before beginning the sampling. Optimal pressures or timing for the start of the sampling may therefore further increase the accuracy of the present method.

As a consequence of the fact that there is an ascending and a descending portion of the calibration curve, there are usually at least two solutions or calendar age ranges possible for any given wine sample. The narrowest probability distributions can be obtained for a wine from 1963 (peak maximum, only one solution) whereas distributions get broader as the bomb peak flattens out over time (compare the probability distributions in FIGS. 7A and 7B). As a consequence, the radiocarbon dating technique described here is most accurate around 1963 and for high precision $F^{14}C$ values.

Figure 8:
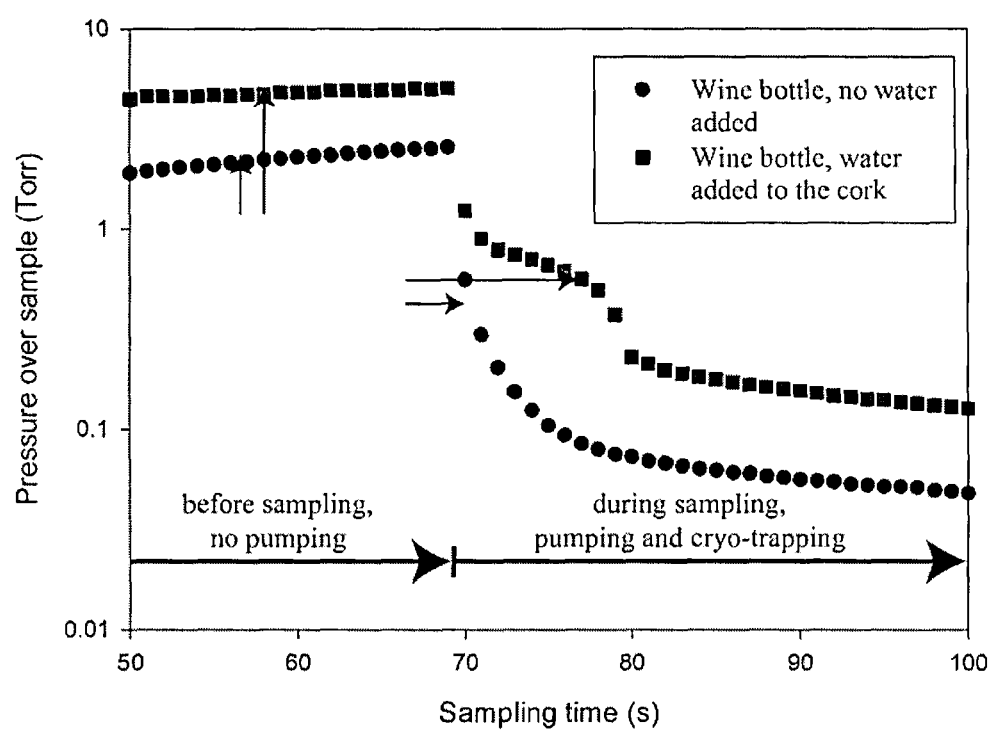
FIG. 8 is a graph that compares a wine sample (1977 Robert Mondavi Cabernet Sauvignon, Reserve) with and without the addition of 10 µl of water placed on top of the cork. Samples with liquid added show higher pressure after the initial pumping phase and exhibit a bump upon pumping and trapping.

Efforts to circumvent the disclosed authentication method by the addition of wine or other organic compounds of the same radiocarbon age as the indicated year of the vintage on the wine label could be detected by monitoring the pressure over the wine during sampling. If liquid was added to the cork or the space between the cork and the foil capsule, the achievable pressure over the bottle would be significantly higher before the sampling and an atypical pressure drop would be observed during the sampling. This was demonstrated by tests shown in FIG. 8, in which two pressure curves were recorded for a wine bottle (1977 Robert Mondavi Cabernet Sauvignon) sampled with and without the addition of 10 μl of water placed on top of the cork. The sample with added water shows a higher than normal pressure when the vacuum was first applied to the bottle, and the liquid being pumped away forms a "bump" in the pressure curve that should normally follow an exponential decay.

Also, small amounts of purposefully-added carbon contamination are not likely to succeed in thwarting the radiocarbon authentication method described here because the added carbon contamination must compensate for cork-sorbed carbon (with the fraudulent radiocarbon value) in order to achieve the correct radiocarbon value. However, because the amount of cork-sorbed carbon is not known before sampling, it is virtually impossible to solve the mass balance equation needed to achieve the correct radiocarbon age of the mix. Adding large amounts of liquid contaminant to overwhelm the fraudulent signal would result in grossly anomalous pressure curves as described above.

While δD measurements of closed bottles are feasible by NMR, $δ^{13}C$ and $δ^{18}O$ measurements are not possible with the same method due to the net zero nuclear spin of $^{12}C$, $^{16}O$ and $^{18}O$. However, stable isotope ratio measurements of ethanol or other molecules of sufficient abundance can also be analyzed in the same vapor and gasses that are extracted from wine bottles for radiocarbon dating using the bottle coupling device 22. For detection of wine fraud, isotopic measurements (e.g., $δ^{13}C$, $δ^{18}O$, δD) are complementary to radiocarbon dates because they permit the ability to determine the following information: wine quality, geographical origin, type of grape and adulteration by the addition of water, sugar, or alcohol. Previous work that examined $δ^{13}C$ and radiocarbon dates of wine ethanol was able to distinguish between several regions of wine production in France. However, these data could only be obtained by opening wine bottles and measuring the liquid directly. Thus, using the bottle coupling device 22 to measure radiocarbon and stable isotope ratios in vapors from intact, closed wine bottles provides a critical means for the authentication of fine and rare wines.

A number of chemical compounds such as acetic acid, acetaldehyde, 4-ethylphenol and geosmin are associated with wine spoilage or wine fault and their presence in wine can be problematic even at very low concentrations. Therefore, detection of these compounds even at low levels may indicate wine spoilage. Similar to the main constituents of wine, these molecules will permeate the cork and can be desorbed from the cork just like water and ethanol. The described vacuum desorption for wine traces may therefore also be used for the detection of wine spoilage or wine faults by the chemical characterization of the desorbed vapors. Sufficient sample sizes can be achieved in a shorter time than for radiocarbon measurements as conventional mass spectrometry does not require micrograms of analytes and measurements can be done either offline or online. In an offline mode, samples would be stored in appropriate vials whereas online sampling could be achieved by transporting a portion of the vapors through a short, heated gas capillary into the ion source of a mass spectrometer. The capillary reduces the pressure further to meet the requirements of the mass spectrometer while heating of the capillary ensures the volatility of compounds throughout the gas capillary. An electron impact (EI) ion source in conjunction with a triple quadrupole mass spectrometer would be an ideal system to identify pre-selected spoilage markers in multiple reaction mode where pre-selected masses of molecular ions are fragmented in a collision cell and characteristic fragments of compounds related to spoilage and wine faults can be detected. By normalizing the signals to the signal of ethanol, semi-quantitative information about the contamination levels can be obtained.

It is also noted that the disclosed systems and methods can be used to detect 2,4,6-trichloroanisole (TCA), which is a very potent compound that causes cork taint in wines. Concentrations as low as 10 parts per trillion (ppt) have been shown to have a perceivable effect in wines. TCA is produced by both microbial and chemical mechanisms either in the cork itself or outside of the bottle and contamination with TCA varies with every cork and every wine bottle. The sample sizes that can be achieved with the disclosed systems and methods are relatively large because of the strong vacuum and trapping method as well as the longer sampling times. Hence, analysis of TCA with the proposed direct coupling of a triple quadrupole mass spectrometer to the bottle coupling device 22 may be achieved without the need for a separate extraction and a gas chromatographic separation. Alternatively, the cryogenically sampled compounds may be allowed to warm up in a closed volume connected to the MS/MS setup in order to allow higher concentrations of analytes such as TCA in the gas phase.

Figure 9:
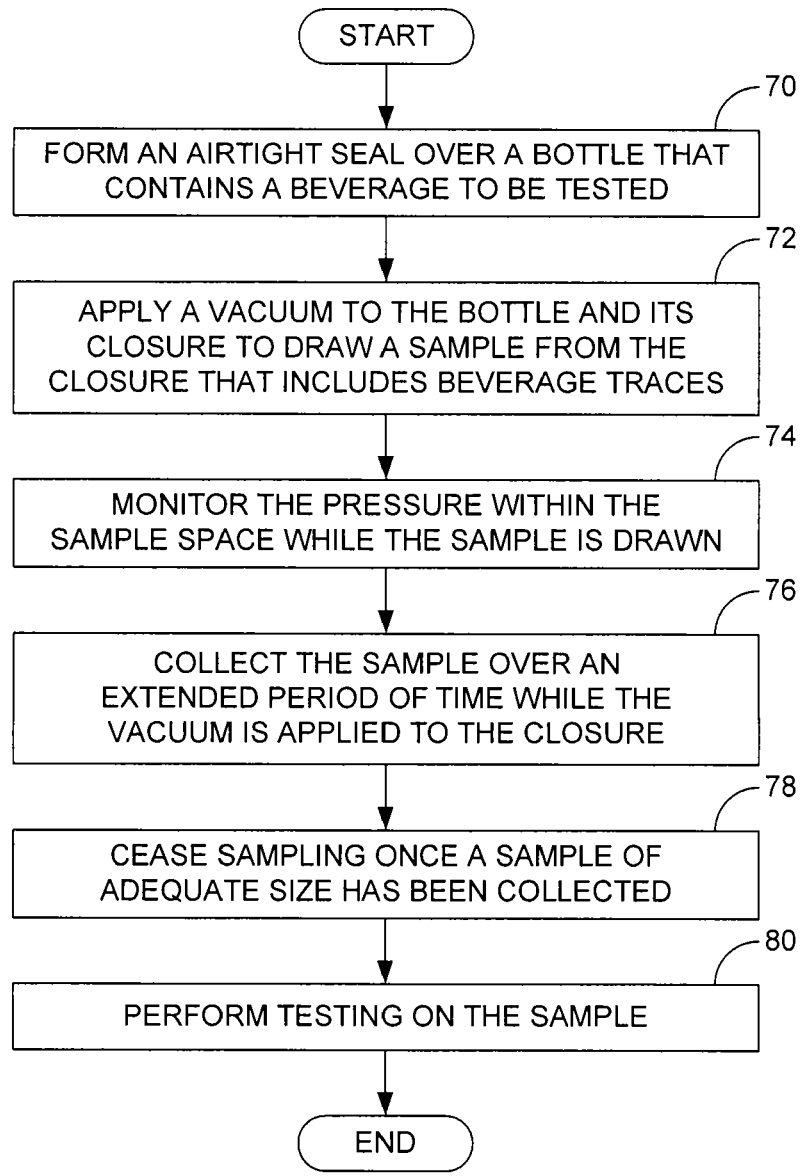
FIG. 9 is a flow diagram of an embodiment of a method for non-invasively and non-destructively authenticating a bottled beverage.

FIG. 9 is a flow diagram that summarizes an example method for non-invasively and non-destructively authenticating a bottled beverage that is consistent with the foregoing disclosure. Beginning with block 70, an airtight seal is formed with a bottle that contains a beverage to be tested. As noted above, the seal can be formed with a beverage coupling device, such as that illustrated in FIGS. 3 and 4.

Referring to block 72, a vacuum is applied to the bottle and its closure (e.g., a cork closure) to draw a sample from the closure that includes traces of the beverage contained in the bottle. In some embodiments, a relatively strong vacuum is applied. For example, a vacuum of approximately 0.5 Torr is initially applied to the closure. In some embodiments, this pressure is reached after about only one second of sampling. Because the pressure of the sample space with the coupling device will change as molecules are drawn from the closure, the pressure within the sample space is monitored while the sample is drawn, as indicated in block 74. In some embodiments, it is necessary to maintain a relatively strong vacuum during the sampling process to remove the beverage traces from the closure. If the vacuum were not strong enough or were not applied continuously, the system would reach an equilibrium between desorption and re-adsorption at low analyte concentrations and the sample sizes would not be sufficient for radiocarbon or stable isotope ratio measurements. In some embodiments, the sample space is maintained at a pressure of approximately 0.5 to $10^{-3}$ Torr during sampling, which is achieved by continuously pumping with the vacuum pumps and the cryotrap.

With reference to block 76, the sample is collected over an extended period of time while the vacuum is applied to the closure. An extended time period is necessary to draw samples of adequate size for radiocarbon and stable isotope ratio measurements. By way of example, the sample can be collected for a period of approximately 30 to 120 minutes. In some embodiments, the sample is collected using cryogenic trapping, which enables the collection of virtually all beverage constituents in quantities from single molecules to grams.

Referring next to block 78, sampling is ceased once a sample of adequate size has been collected. In some embodiments, whether or not an adequate sized sample has been collected can be determined in relation to the monitored pressure of the sample space (which identifies the quantity of material being removed from the closure) and the duration of time the sample space has been maintained at that pressure.

Once a sample of adequate size has been collected, it can be tested, as indicated in block 80. If the sample was collected using cryogenic trapping, the sample can be transferred from the cryotrap to a glass tube, which can then be closed to form a sealed ampoule. As described above, the testing can comprise radiocarbon testing to estimate the age of the beverage or evaluation of stable isotope ratios to estimate other characteristics of the beverage, such as quality, geographical origin, type of grape, or adulteration. In other embodiments, the sample can be tested to detect the presence of one or more compounds that can cause wine spoilage, such as acetic acid, acetaldehyde, 4-ethylphenol, geosmin, or 2,4,6-trichloroanisole (TCA).

The invention claimed is:

1. A system for authenticating bottled beverages, the system comprising:
    a bottle coupling device adapted to form an airtight seal with a neck and closure of a bottle that contains a beverage to be authenticated;
    a vacuum line in fluid communication with the bottle coupling device; and a vacuum pump in fluid communication with the vacuum line, the pump being adapted to develop a vacuum along the vacuum line and within the bottle coupling device so as to apply a vacuum to the closure of the bottle and draw traces of the beverage that have diffused through the closure.

2. The system of claim 1, wherein the bottle coupling device comprises a hollow body that is adapted to fit around the neck of the bottle, the body defining an interior space in which the bottle can be inserted.

3. The system of claim 2, wherein the bottle coupling device further comprises a sample line that is in fluid communication with the interior space and the vacuum line.

4. The system of claim 3, wherein the bottle coupling device further comprises a vent line that is in fluid communication with the interior space.

5. The system of claim 4, wherein the bottle coupling device further comprises a coupler positioned at an end of the sample line that couples the device to the vacuum line.

6. The system of claim 2, wherein the bottle coupling device further comprises a resilient sealing member positioned at an opening to the interior space of the body.

7. The system of claim 1, further comprising a pressure sensor in fluid communication with the vacuum line that is adapted to measure the vacuum applied to the closure.

8. The system of claim 1, further comprising a cryotrap in fluid communication with the vacuum line that is adapted to collect a sample that includes the beverage traces.

9. The system of claim 8, further comprising a quartz glass tube in which the collected sample can be placed and sealed.

10. A bottle coupling device adapted to form an airtight seal with a neck and closure of a bottle, the device comprising:
    a hollow body that is adapted to fit around the neck of the bottle, the body defining an interior space in which the bottle can be inserted;
    a sample line that is in fluid communication with the interior space;
    a vent line that is in fluid communication with the interior space; and
    a coupler positioned at an end of the sample line that is adapted to couple the sample line to a vacuum line of a sampling system.

11. The device of claim 10, further comprising a resilient sealing member positioned at an opening to the interior space of the body.

12. The device of claim 11, further comprising a collar provided on the body that is adapted to retain the sealing member.

13. A method for evaluating a beverage, the method comprising:
    forming an airtight seal with a bottle that contains the beverage, the bottle being sealed with a closure;
    applying a vacuum to the bottle to draw a sample from the closure that includes traces of the beverage that have diffused through the closure;

collecting the sample while the vacuum is applied to the closure; and performing testing on the collected sample.

14. The method of claim 13, wherein forming an airtight seal comprises forming the airtight seal with the bottle using a bottle coupling device including a hollow body that is adapted to fit around a neck of the bottle, a sample line that is in fluid communication with an interior space of the body, and a coupler positioned at an end of the sample line that is adapted to couple the sample line to a vacuum line of a sampling system.

15. The method of claim 13, wherein applying a vacuum comprises initially applying a pressure of approximately 0.5 Torr to the closure.

16. The method of claim 13, wherein applying a vacuum comprises maintaining a pressure of approximately 0.5 to $10^{-3}$ Torr while the sample is collected.

17. The method of claim 16, wherein maintaining a pressure comprises continuously pumping with a vacuum pump in fluid communication with the closure.

18. The method of claim 13, wherein collecting the sample comprises collecting the sample for a period of approximately 30 to 120 minutes.

19. The method of claim 13, wherein collecting the sample comprises collecting the sample using a cryotrap.

20. The method of claim 13, wherein performing testing comprises radiocarbon testing the sample to estimate the age of the beverage.

21. The method of claim 13, wherein performing testing comprises evaluating stable isotope ratios to estimate one or more characteristics of the beverage.

22. The method of claim 13, wherein performing testing comprises performing chemical analysis on the sample to estimate a quality of the beverage.

23. The method of claim 13, further comprising measuring the vacuum to evaluate a quality of the closure.

* * * * *